United States Patent [19]

Larkin

[11] Patent Number: 5,215,538
[45] Date of Patent: Jun. 1, 1993

[54] CONNECTOR-ACTIVATED IN-LINE VALVE

[75] Inventor: Mark E. Larkin, Lindenhurst, Ill.

[73] Assignee: Abbott Laboratories, Abbott Park, Ill.

[21] Appl. No.: 831,726

[22] Filed: Feb. 5, 1992

[51] Int. Cl.⁵ ............................................. A61M 5/00
[52] U.S. Cl. ...................................... 604/249; 604/283; 137/516.13; 137/859; 251/149.1
[58] Field of Search .................... 604/30, 33, 89–91, 604/246, 249, 283, 905, 247, 9, 256; 251/149, 149.1, 149.6; 137/516.13, 516.17, 852, 859

[56] References Cited

U.S. PATENT DOCUMENTS

| | | | |
|---|---|---|---|
| 3,726,282 | 4/1973 | Patel | 251/149.6 |
| 4,344,435 | 8/1982 | Aubin | 604/246 |
| 4,397,442 | 8/1983 | Larkin | 251/342 |
| 4,421,296 | 12/1983 | Stephens | 251/149.7 |
| 4,654,033 | 3/1987 | Lapeyre et al. | 604/175 |
| 4,683,916 | 8/1987 | Raines | 137/854 |
| 4,712,583 | 12/1987 | Pelmulder et al. | 137/852 |
| 4,874,377 | 10/1989 | Newgard et al. | 604/167 |
| 4,904,236 | 2/1990 | Redmond et al. | 604/9 |
| 4,915,687 | 4/1990 | Sivert | 604/83 |
| 5,041,087 | 8/1991 | Loo et al. | 604/83 |

*Primary Examiner*—C. Fred Rosenbaum
*Assistant Examiner*—Corrine Maglione
*Attorney, Agent, or Firm*—Thomas M. Breininger

[57] ABSTRACT

An in-line valve for a medical tubing set has a tubular member characterized by an internal annular valve seat and a generally circular rubber-like valve member disposed transversely of the tubular member with its edges fixed relative thereto and with a central portion thereof tensioned into seating engagement against the annular valve seat whereby to normally close the in-line valve. Elements on the valve member are engageable by a connector as same is assembled to the tubular member to move the valve member off of the valve seat whereby to automatically open the in-line valve upon assembly of a connector thereto.

9 Claims, 2 Drawing Sheets

CONNECTOR-ACTIVATED IN-LINE VALVE

BACKGROUND OF THE INVENTION

In assembling medical tubing sets for administering medicaments, nutrients and other solutions to patients, there may be situations in which it would be desirable to have a valve connected to the end of a catheter or medical tubing which is normally closed but which valve is automatically opened upon assembly of a connector mounted on the end of another tubing thereto.

SUMMARY OF THE INVENTION

The present invention is directed to such an in-line valve which is normally closed but which is automatically opened by a connector being assembled thereto. Upon disassembly of the connector from the valve, it closes automatically. Thus, leakage from the valve is minimized during connections thereto and disconnections therefrom.

This new and novel valve is characterized by first and second tubular members which are secured together so as to define a longitudinally extending flow path therethrough and an annular valve seat therebetween, a second valve seat provided on one of the tubular members and disposed transversely to the aforesaid flow path, a circular rubber-like valve member disposed transversely of the aforesaid flow path with its peripheral edge retained in the annular valve seat and with its central portion seated in tension against said second valve seat whereby the subject in-line valve is normally closed. Engageable means are provided on the rubber-like valve-member for engagement by a connector being assembled to the in-line valve to move the valve member off of the second valve seat and thus to automatically open the in-line valve. The in-line valve and the connector may have mating luer tapers whereby to provide a non-sticking connection.

The present invention is directed to a new and improved in-line valve for a medical tubing set wherein the normally closed valve is automatically opened upon assembly of a connector thereto.

An object of the present invention is to provide a new and improved in-line valve for a medical tubing set wherein a tubular member having a flow path therethrough is normally closed by a rubber-like valve member which extends transversely across the flow path and in tension against a valve seat and wherein a connector, during assembly to the tubular member, is engageable with portions of the rubber-like valve member so as to move same off of the valve seat and automatically open the flow path therethrough.

Another object of the present invention is to provide such a new and improved in-line valve wherein a non-sticking luer connection is provided between the tubular valve member and the connector.

BRIEF DESCRIPTION OF THE DRAWINGS

The features which are believed to characterize this invention are set forth in the appended claims. The invention itself, together with its features, objects and attendant advantages, will be best understood by reference to the following detailed description of the presently preferred embodiments thereof, taken in conjunction with the accompanying drawings, in which:

DESCRIPTION OF PREFERRED EMBODIMENTS

Figure 1:
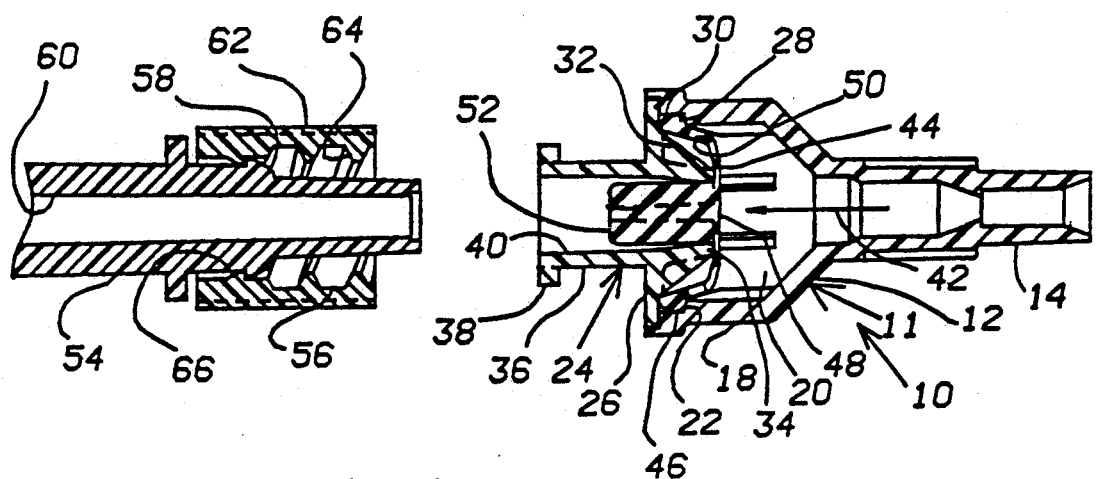
FIG. 1 is a side elevational view, in longitudinal section, of an in-line valve for a medical tubing set embodying the invention and showing a connector about to be assembled thereto.
Figure 2:
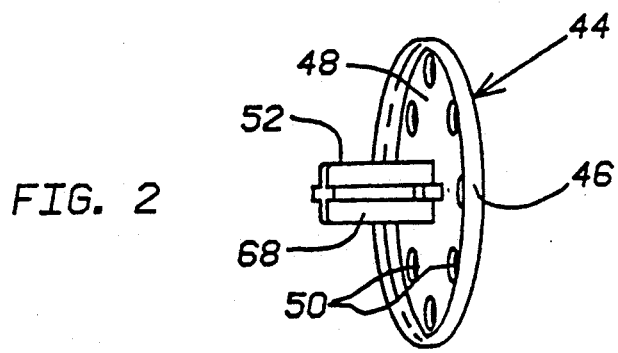
FIG. 2 is a perspective view of the circular rubber-like valve member of FIG. 1.
Figure 3:
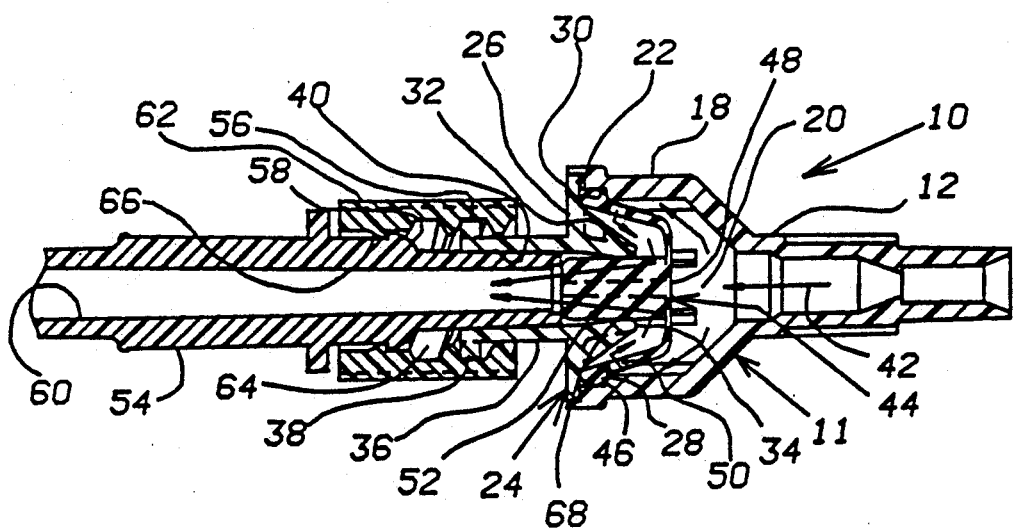
FIG. 3 is a view similar to FIG. 1 after assembly of the connector to the in-line valve and illustrating automatic opening of the valve.

Referring now to the drawings, a first preferred embodiment of the invention, as shown in FIGS. 1-3, comprises an in-line valve 10 which is characterized by a two-part generally tubular body member 11 including a first tubular member 12 having a first end 14. The other end 18 of the first tubular member 12 is enlarged and sealingly secured to an annular flange 26 on a second generally tubular member 24 whereby to define a valve chamber 20 in the tubular body member 11 and a fluid flow path 42 therethrough.

Spaced apart shoulder formations 22 and 28 on the first and second tubular members 12 and 24, respectively, define an annular groove 30 on the inner surface of the chamber 20, the purpose for which will be made clear hereinafter. The second tubular member 24 is further characterized by a tubular projection 32 into the valve chamber 20 which defines an annular valve seat 34 which is disposed inwardly of the annular groove 30 in the chamber 20.

A tubular body portion 36 of the second tubular member 24 extends longitudinally away from the first tubular member 12 in axial alignment with the first end 14 of the first tubular member 12 and has an external thread formation 38 at its other end. In this preferred embodiment, the tubular body portion 36 of the second tubular member 24 is provided with a luer-taper bore 40 for a purpose that will be discussed hereinafter.

As best illustrated in FIG. 2, a circular, rubber-like resilient valve member 44 is disposed in the valve chamber 20 transversely of the flow path 42 therethrough. Suitable materials from which the resilient valve member 44 could be formed would include silicon, latex and thermoplastic rubbers. The valve member 44 has an enlarged or rolled peripheral edge 46 which, during assembly of the two tubular members 12 and 24, is fixedly and sealingly trapped in the annular groove 30 by the shoulders 22 and 28 and the tubular projection 32 of the second tubular member 24, a central portion 48 of the resilient valve member 44 being tensioned across and in sealing engagement with the annular valve seat 34, as illustrated in FIG. 1, thus normally blocking the flow path 42 and closing the in-line valve 10. As best shown in FIG. 2, a series of circumferentially arranged flow holes 50 are provided in the resilient valve member 44 outwardly of the sealing engagement thereof with the annular valve seat 34. The flow holes 50 provide fluid passage means past the valve member 44 when the valve member 44 is displaced from its normal sealing engagement with the annular valve seat 34.

As the in-line valve 10 is to be automatically opened when a connector, such as connector 54 in FIG. 1, is assembled to the in-line valve 10, abutment means engageable by the end of the connector 54 are provided on the valve member 44. As illustrated in FIG. 2, the abutment means for this embodiment is a projecting member 52 formed integrally on the center of the valve member 44 which projects into the bore 40 of the second tubular member 24 with the end thereof being engageable by the end of the connector 54 as it is assembled to the in-line valve 10 whereupon the valve member 44 is moved off of the annular valve seat 34 and the in-line valve 10 is automatically opened with the flow path 42 being, as shown by the arrows in FIG. 3, from the valve chamber 20, through the flow holes 50, past the valve seat 34, and through passageways 68 into the bore 60 of the connector 54, which may be fitted on the end of a patient's in-dwelling catheter, for instance. The connector 54 has a mating luer-taper on its outer surface, as at 56, whereby the connection between the connector 54 and the second tubular member 24 of the in-line valve 10 is a non-sticking connection. The projecting member 52, in this embodiment, has an cross-shaped transverse cross-section whereby to define the passageways 68 therepast. Upon disassembly of the connector 54 from the in-line valve 10, the tensioned valve member 44 is automatically biased back into sealing engagement with the annular valve seat 34.

The connector 54 is secured to the in-line valve 10 by a lock nut 62 which is rotatable on the connector 54 but which has an internal thread formation 64 which is rotatably engageable with the thread formation 38 provided on the outer end of the second tubular member 24, as best illustrated in FIG. 3. The connector 54 is longitudinally movable with the lock nut 62 through engagement of an internal annular driving flange 66 on the lock nut 62 with an external mating annular flange 58 provided on the connector 54.

One example of the benefits from the use of the connector-activated in-line valve 10 of the present invention would be where the medical tubing 16 were connected to an in-dwelling catheter of a patient requiring a continuing supply of nutrient, medicament, etc. When the reservoir bag or other source approaches the empty or warning point, a nurse or other medical technician merely untightens the lock nut 62, disassembling the supply connector 54 from the in-line valve 10 which automatically closes until the connector of a fresh supply bag is quickly and neatly assembled to the in-line valve 10 which automatically opens so as to minimize the interruption of treatment to the patient. Spillage is minimized as is the fumbling with clamps on the patient side of the in-line valve 10. In this instance, the flow arrows in FIG. 3 would be reversed. As the connector-activated in-line valve 10 may be used in place of a sharp needle/rubber reseal arrangement, it also serves to provide an important safety feature, particularly as to medical technicians working therewith.

Figure 4:
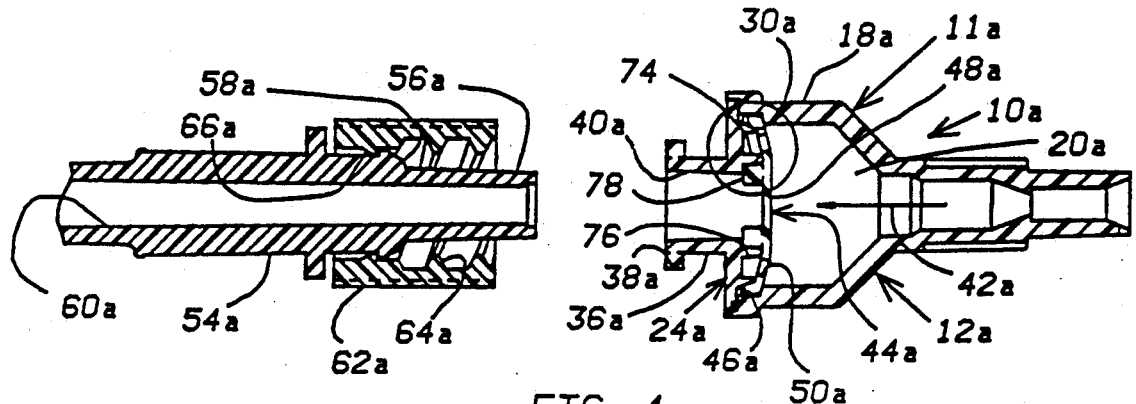
FIG. 4 is a side elevational view, in longitudinal section, similar to FIG. 1 of another embodiment of the invention.
Figure 5:
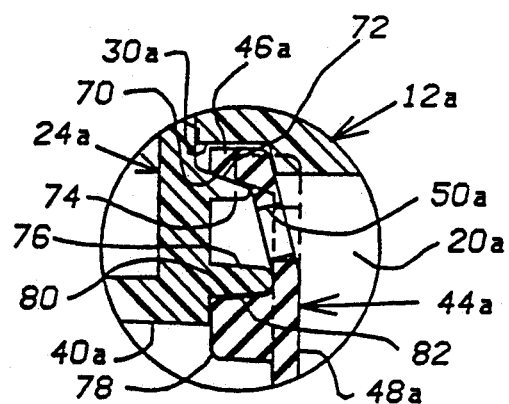
FIG. 5 is an enlarged detail view of the portion of FIG. 4 circled.
Figure 6:
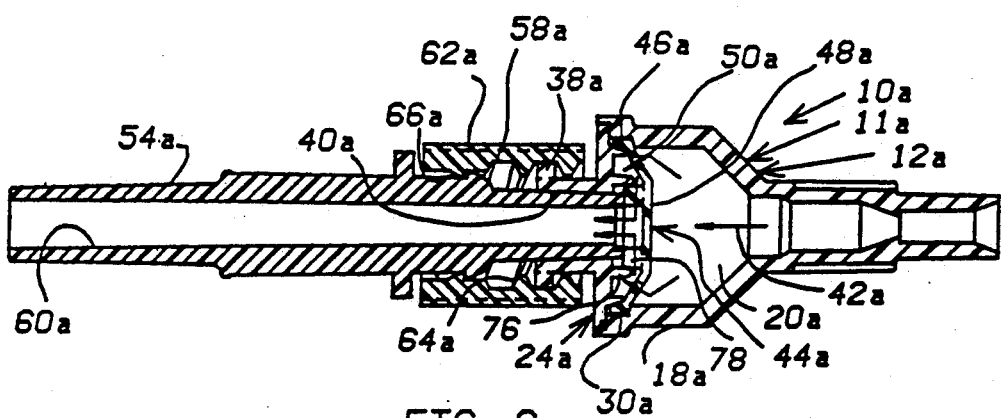
FIG. 6 is a view similar to FIG. 3 of the embodiment of the invention shown in FIGS. 4 and 5.

Another preferred embodiment of an in-line valve of the invention is illustrated in FIGS. 4–6. Elements identical or quite similar to those of the embodiment of FIGS. 1–3 will be identified on the drawings by the same reference numerals with the suffix "a". In this embodiment, the first tubular member 12a is quite similar to the first tubular member 12 of the first described embodiment but the second tubular member 24a has some modifications associated therewith including a shorter tubular body portion 36a. The circular resilient valve member 44a is also modified in that the peripheral edge 46a thereof is more flange-like in configuration and is directed toward the second tubular member 24a. It also has an inclined inner surface 70 which is complementary to an inclined outer surface 72 provided on an annular ridge 74 on the second tubular member 24a which projects into the valve chamber 20a. As best illustrated in FIG. 5, when the two tubular members 12a and 24a and the resilient valve member 44a are assembled together, the inclined surface 72 on the ridge 74 engaging the inclined surface 70 on the flange-like peripheral edge of the valve member 44a effectively serves to position and fixedly and sealingly retain said flange-like peripheral edge in the annular groove 30a (FIG. 5).

The annular valve seat engageable by the tensioned resilient valve member 44a is defined by an annular ring 76 which extends a shorter distance into the valve chamber 20a than the tubular projection 32 of the first embodiment. The annular ring 76 projects into the valve chamber 20a from the second tubular member 24a radially outwardly of the inner end of the luer-taper bore 40a thereof. In this embodiment, the abutment means integrally provided on the resilient valve member 44a are in the form of a series of circumferentially spaced abutments 78 which, when the valve member 44a is in its normal tensioned sealing engagement with the annular ring valve seat 76, are engageable with the second tubular member 24a at the inner end of the bore 40a thereof, the outer surfaces of the abutments 78 being slightly tapered, as at 80 (FIG. 5), and slideably engageable with the inner surface of the valve seat ring 76 which is also slightly tapered as at 82 (FIG. 5).

The connector 54a and lock nut 62a operate in the same previously described manner to assemble the connector 54a to the in-line valve 10a with the inner end of the connector 54a being engageable with the abutments 78, as shown in FIG. 6, to move the valve member 44a off of the valve seat ring 76 and thus automatically open the in-line valve 10a and permit fluid flow from the valve chamber 20a through the flow holes 50a in the valve member 44a and past the valve seat ring 76 and the spaced apart abutments 78 into the bore 60a of the connector 54a. Disassembly of the connector 54a from the in-line valve 10a permits the biased valve member 44a to again sealingly engage the valve seat ring 76 and automatically close the in-line valve 10a, as previously described in connection with the first embodiment.

While there has been shown and described two possible embodiments of the invention, it will be obvious to those skilled in the art that further changes and modifications may be made without departing from the invention, and it is intended by the appended claims to cover all such changes and modifications as fall within the true spirit and scope of this invention.

I claim:

1. A connector-activated in-line valve comprising, a generally tubular body member having an inner surface, an internal annular valve seat provided intermediate the opposite ends of said tubular body member, a circular resilient rubber-like valve member disposed in said tubular body member and having its peripheral edge sealingly fixed relative to said inner surface thereof so as to normally prevent any liquid flow through said tubular body member and having flow holes provided therein outwardly of its engagement with said annular valve seat, a central portion of said valve member being stretched in tension across said annular valve seat, and means on said valve member comprising an elongated member which projects longitudinally of said tubular member from the center of said valve member with a free end thereof being engageable by a connector being assembled to said tubular body member to move said valve member off of said valve seat said elongated member defining fluid passage means therepast, whereupon said in-line valve is automatically opened when a connector is assembled to said tubular body member and automatically closed when a connector is disassembled from said body member as a result of the tensioned rubber-like valve member being released and reseating itself on said annular valve seat.

2. The in-line valve of claim 1 wherein said engageable valve member means comprises a series of circumferentially spaced abutments integrally formed on said valve member and adapted for valve-opening engagement by an annular end of a connector during assembly of same to said tubular body member.

3. The in-line valve of claim 1 wherein said generally tubular body member comprises an inlet member and an outlet member secured together, wherein said peripheral edge of said valve member is sealingly fixed between said inlet and outlet members, and wherein said annular valve seat is provided on said outlet member.

4. The in-line valve of claim 3 wherein said outlet member is characterized by a luer-taper bore.

5. A connector-activated in-line valve comprising, a two-part generally tubular body member, an internal annular valve seat provided on one of said member parts intermediate the opposite ends of said tubular body member, a circular resilient rubber-like valve member disposed in said tubular body member and having its peripheral edge fixed relative thereto and its central portion stretched in tension across said annular valve seat so as to prevent any liquid flow through said tubular body member whereupon said in-line valve is normally closed, and a projection on said valve member which is movable by a connector being assembled to said tubular body member in a direction such that said valve member is moved off of said valve seat, said in-line valve being automatically opened when a connector is assembled to said two-part tubular body member and automatically closed when a connector is disassembled from said body member as a result of the tension rubber-liked valve member being released and reseating itself on said annular valve seat.

6. A connector-activated in-line valve comprising, a first generally tubular body member having one end connected to the end of a length of plastic tubing and with the other end having an enlarged bore with first shoulder means disposed inwardly of said other end thereof, a circular resilient rubber-like valve member disposed in said enlarged bore of said first body member and having an enlarged edge seated against said first shoulder means, and a second generally tubular body member having an inner end and closing said other end of said first body member and having second shoulder means for retaining said enlarged edge of said valve member against said first shoulder means and an annular valve seat at its inner end which engages and tensions a central portion of said valve member to normally close said in-line valve, said valve member having a series of flow holes therein which are disposed outwardly of the engagement thereof with said annular valve seat and a centrally disposed portion which projects into said second tubular body member and is engageable and movable by a connector being assembled to said second body member whereby said valve member is moved off of said valve seat and said in-line valve is therefore automatically opened, said projecting portion defining fluid passage means therepast, disassembly of said connector from said second body member resulting in automatic closing of said in-line valve due to the disengagement of said connector from said projecting portion and the tension of said resilient valve member.

7. The in-line valve of claim 6 wherein said centrally disposed projecting portion comprises a longitudinally disposed member which extends into said second body member from the center of said valve member and which has a generally cross-shaped transverse cross-section.

8. The in-line valve of claim 6 wherein said centrally disposed projecting portion comprises a series of circumferentially spaced abutments which extend toward the interior of said second body member from said valve member, said abutments being disposed radially inwardly of the tensioned engagement of said valve member with said annular valve seat.

9. The in-line valve of claim 6 wherein said second tubular member is further characterized by a luer-taper.

* * * * *

UNITED STATES PATENT AND TRADEMARK OFFICE
CERTIFICATE OF CORRECTION

PATENT NO. : 5,215,538
DATED     : June 1, 1993
INVENTOR(S) : Mark E. Larkin

It is certified that error appears in the above-identified patent and that said Letters Patent is hereby corrected as shown below:

Column 5, line 43, replace "tension" with --tensioned--

Column 5, line 44, replace "rubber-liked" with --rubber-like--

Signed and Sealed this

First Day of March, 1994

Attest:

BRUCE LEHMAN

Attesting Officer

Commissioner of Patents and Trademarks